United States Patent [19]

Gryczka et al.

[11] 4,304,868
[45] Dec. 8, 1981

[54] **PROCESS FOR THE TREATMENT OF MEAT WITH COMPOSITIONS INCLUDING *MICROCOCCUS VARIANS* AND A LACTIC ACID PRODUCING BACTERIA**

[75] Inventors: Alfred J. Gryczka, Sarasota; Ramesh B. Shah, Bradenton, both of Fla.

[73] Assignee: Microlife Technics, Inc., Sarasota, Fla.

[21] Appl. No.: 931,315

[22] Filed: Aug. 7, 1978

Related U.S. Application Data

[62] Division of Ser. No. 830,917, Sep. 6, 1977, Pat. No. 4,147,807.

[51] Int. Cl.$^3$ ............................................. C12N 1/20
[52] U.S. Cl. ................................... 435/253; 426/56; 435/42; 435/822; 435/859
[58] Field of Search ................... 435/42, 68, 69, 253, 435/859, 822; 426/56, 58, 59

[56] References Cited

U.S. PATENT DOCUMENTS

| | | | |
|---|---|---|---|
| 1,380,068 | 5/1921 | Kurk | 426/56 |
| 3,193,391 | 7/1965 | Jansen et al. | 426/56 |
| 3,561,977 | 2/1971 | Rothchild et al. | 426/59 |
| 3,975,545 | 8/1976 | Vedamuthu | 426/40 |
| 4,013,797 | 3/1977 | Gryczka | 426/56 |
| 4,147,807 | 4/1979 | Gryczka et al. | 426/56 |

FOREIGN PATENT DOCUMENTS 1692174  3/1972  Fed. Rep. of Germany ........ 426/56

OTHER PUBLICATIONS

F. P. Niinivaara et al., Food Technology, vol. 18, No. 2, pp. 25-31, 1964.

*Primary Examiner*—Robert J. Warden
*Attorney, Agent, or Firm*—Ian C. McLeod

[57] ABSTRACT

An improved process for producing a superior flavor in fermented meat, particularly sausage, using *Micrococcus varians* in admixture with *Pediococcus cerevisiae* NRRL-B-5627 and/or with other lactic acid producing meat fermenting bacteria for lowering the pH is described. *Micrococcus varians* is a very poor producer of lactic acid and alone cannot produce acceptable sausage. The improved bacterial compositions develop the solid bright red color associated with sausage and other fermented meats in the presence of edible nitrate and/or edible nitrite. Combinations of the nitrite and nitrate can be used. No acid forming chemicals, such as gluconic acid delta lactone, are used in the fermentation process. The bacterial composition is preferably provided in the form of a frozen cell concentrate for storage and subsequent thawing for use.

5 Claims, No Drawings

PROCESS FOR THE TREATMENT OF MEAT WITH COMPOSITIONS INCLUDING *MICROCOCCUS VARIANS* AND A LACTIC ACID PRODUCING BACTERIA

This is a division of application Ser. No. 830,917 filed Sept. 6, 1977 now U.S. Pat. No. 4,147,807.

SUMMARY OF INVENTION

This invention relates to the process for developing an improved flavor in fermented meat particularly in dry or semi-dry sausages using a bacterial composition of *Micrococcus varians* along with *Pediococcus cerevisiae* NRRL-B-5627 and/or other lactic acid producing meat fermenting bacteria for lowering the pH and also developing a uniform solid bright red color in the sausage in the presence of edible nitrate and/or nitrite. It also relates to the bacterial concentrates which produce this result.

PRIOR ART

Processes for dry and semi-dry sausage preparation are examples of conventional fermentations where acidity is generated to provide tang. Dry and semi-dry sausages vary in taste according to the meat source, i.e., pork, beef, veal, etc. and their different mixtures, and the sugar and spices etc. and their different mixtures, and the sugar and spices used in processing. The fairly distinct categories of semi-dry sausage are known as summer sausage, cervelat, Thuringer, pork roll and lebanon bologna. Some dry sausages are Chorizos, hard salami, Genoa salami, German katenwurst and Mettwurst salamis, and various kinds of Italian sausage such as Pepperoni and Cappicola. There are other dry and semi-dry sausages which are produced by the present invention.

Dry and semi-dry sausages are generally distinguished from other types of sausages by the prior art in that they are fermented. The comminuted meat mixture, which may or may not first be cured, is mixed with added salt, spices, edible nitrite and/or nitrate and optionally with an enediol reducing agent, bacteria and sometimes acid forming chemicals. It is then stuffed into casings and fermented with the bacteria. Curing allows the edible nitrites, and nitrates upon subsequent reduction to nitrite, to form nitric oxide which in the presence of acids combines with the pigment in the meat to produce the red color usually associated with the sausage. It is the edible nitrites which generate the red color in the meat and more importantly which provide protection against the formation of botulism toxin by *Clostridium botulinum* growth.

The fermented sausage may be given a light or heavy smoke. The semi-dry sausages are normally cooked after the fermentation without an extensive drying period. The dry sausage is dried for various time periods under controlled humidity and temperature conditions, depending upon the nature of the end product. Because of this processing, the resulting sausages differ from other types of sausage, such as fresh, smoked, cured, cooked and the so-called new condition sausages.

A commonly used starter bacterium for fermenting meat to produce semi-dry sausage is *Pediococcus cerevisiae* because it rapidly produces large amounts of primarily lactic acid to lower the pH, which gives the final sausage its characteristic tang. This bacterium is commercially obtainable both in a frozen state as a concentrate and in a lyophilized state. It may be for instance the bacterium described in U.S. Pat. No. 3,561,977.

Species of Micrococcus are also used in making sausage, particularly in German. W. German Pat. No. 1,692,174 describes an unidentified strain of Micrococcus mixed with lactic acid forming bacteria, with substantial amounts of gluconic acid delta lactone (GDL) to rapidly lower the pH, and with polyphosphates, ascorbic acid and its sodium salts as pH regulators. GDL has a chemical acid taste and is undesirable for this reason. Possible the Micrococcus is strain M-53 which has now degenerated as described in Food Technology, Vol 18, No. 12, pages 25 to 31 (1964). New Micrococcus strains with high lactic acid producing activity are continuously sought after by the prior art. The Food Technology publication indicates that most Micrococcus isolates tested are not satisfactory for making sausage. The discovery of a satisfactory Micrococcus is a matter of considerable chance as is also shown in the publication. The Micrococcus are shown to be mixed with sodium nitrite which produces the red sausage color during the fermentation as discussed above. Microbiology Vol. 26, No. 4, pp 489 to 496 (1973) and U.S. Pat. No. 1,380,068 describe the importance of the naturally occurring micrococci in the meat on color development. U.S. Pat. No. 4,013,797 also describes the importance of using a high acid producing nitrate reducing bacteria characterized as Micrococssus sp. NRRL-B-8048.

U.S. Pat. No. 3,193,391 describes the use of various flavor producing bacteria from the families Lactobacteriaceae and Micrococcaceae for preparing cured meats. This is a related fermentation process for flavor development on large sized meat sections.

OBJECTS

It is therefore an object of the present invention to provide a process for producing fermented meat with an excellent flavor and color where a particular species Micrococcus which has very poor acid producing characteristics is used contrary to the teachings of the prior art. It is also an object of this invention to provide unique bacterial compositions for use in the process. It is particularly an object of the present invention to provide bacterial concentrates which produce fermented meat wherein the pH and flavor of the fermentate can be varied by using mixtures of bacteria in various ratios. These and other objects will be increasingly apparent by reference to the following description.

GENERAL DESCRIPTION

The invention relates to the improvement in the process of producing of dry and semi-dry sausage and other fermented meat products which comprises fermenting meat with a composition which comprises as the active ingredients *Micrococcus varians* and at least one meat fermenting lactic acid producing bacterium to lower the pH to less than about 5.4 to above about 4.8. Preferably edible nitrite if used to produce a red color is added in an amount less than about 200 ppm.

The bacterial concentrates of the present invention comprise *Micrococcus varians* and between 0.01 and 100 parts by count of a lactic acid producing bacterium which ferments in meat to lower the pH to less than about 5.4 to above about 4.8 per part of Micrococcus wherein the concentrate contains at least about $1 \times 10^9$ bacteria cells per ml and is frozen to less than about $-20°$ C.

As used herein the term "red color" means the color associated with presently marketed fermented sausages and processed meats as accepted in the trade. It is easily distinguished from the gray color of untreated aged meat. Also edible nitrites initially produce a gray color when mixed with meat which changes to a red color over a period of time as is well known to those skilled in the art.

The specific strain of *Micrococcus varians* used in the present invention is available from the Americal Type Culture Collection No. 15,306 and is the neotype strain as described in Bergey's Manual of Determinative Bacteriology (8th Ed., 1974) pages 481 and 482. It is deposited with the USDA Regional Laboratory in Peoria, Ill. as NRRL-B-11,060. It is believed that it has never been suggested by the prior art to use *Micrococcus varians* for any purpose related to meat fermentation. It is unexpected that it could be used to develop a superior flavor in fermented meats.

*Micrococcus varians* is a relatively very poor acid producer. It can produce a red color change in the meat with edible nitrite and/or an edible nitrate. Acid is necessary in the formation of nitric oxide from the nitrite which reacts with components of the meat to form the red color, and thus *Micrococcus varians* is used with selected meat fermenting lactic acid producing bacteria for color change. The use of added acids (such as GDL) is avoided.

A problem with the nitrate reducing bacteria used by the prior art is that the nitrate reductase enzymes are pH sensitive. Acid producing chemicals, such as GDL, cannot be used for this reason. Depending upon the particular species of bacterium, the nitrate reducing activity is terminated when a particular acid level is achieved. With NRRL-B-8048, described in U.S. Pat. No. 4,013,797, this pH is about 5.6; however, NRRL-B-8048 reduces nitrate rapidly enough so that reduction is completed within the time period that the pH is higher than 5.6 in the sausage. Most other Micrococcus are much slower than NRRL-B-8048 in reducing nitrate and if reduction was terminated at about pH 5.6, nitrate would be incompletely reduced. Unexpectedly it has been found that *Micrococcus varians* ATCC 15,306 is not inhibited in its nitrate reducing function until a pH of about 5.2 is achieved and thus is ideally suited for the compositions of the present invention.

The process using the compositions of the present invention is effective in making processed meats (frankfurters, bologna, luncheon meats and the like) where there is limited fermentation over a period of 4 hours or less in addition to fermenting meat to make sausage. The compositions can be used at levels of $10^6$ to $10^8$ bacteria per gram of meat. With processed meats, small but insignificant amounts of acid are generated by fermentation of sugars present in the meat. Thus as used herein "fermentation" includes the action of the compositions of the present invention on sugars or other organic ingredients of the meat along with the chemical change with edible nitrate and/or nitrite which is evidenced by the red color over short periods of time, regardless of whether significant amounts of acid are generated in the meat.

The "gray ring" which is a color defect seen in fully dried sausage, can also be prevented with the compositions of the present invention. The defect is evidenced by a gray ring around the casing. The defect is believed to be caused by accumulations of hydrogen peroxide and the bacterial compositions including *Micrococcus varians* may generate catalase enzyme which destroys the hydrogen peroxide.

*Micrococcus varians* by generating nitrites from the edible nitrates can also help to prevent the growth of botulism toxin bacteria. Smaller amounts of edible nitrites can be used for their initial antimicrobial action in making meat products according to the present invention. *Micrococcus varians* acts to produce a red color in the presence of small amounts of nitrate even in absence of the nitrite and amounts less than about 200 ppm nitrate produce this result. Usually about 50 to 90 ppm nitrite are regarded as necessary as a minimum to initially prevent the growth of botulism bacteria.

In the method of this invention, lactic acid producing bacteria are used such as *Pediococcus cerevisiae*, or *Streptococcus lactis* in combination with *Micrococcus varians*. It has been found that the flavor of dry and semi-dry sausages is particularly improved by using *Pediococcus cerevisiae* as the lactic acid producing bacterium. *Pediococcus cerevisiae* NRRL-B-5627, which is freely available from the USDA, is particularly preferred since it inhibits the development of undesirable putrefying or contaminating bacteria such as *Staphylococcus aureus* as well as rapidly producing lactic acid.

In the process of making sausage, the conventional steps are carried out. Thus, the proper selection of a single meat or different meats is chopped and mixed either separately or together. The next step is that of adding and mixing the curing agents including edible nitrates or edible nitrites or mixtures thereof, salt, dextrose (or other suitable carbohydrates) and spices. This selection and the relative amounts conform to standard practices. The bacterial concentrate is added during the mixing of the other components of the sausage.

In the sausage making process of this invention, a culture composition of *Micrococcus varians* and the lactic acid producing meat fermenting bacteria in an amount between 0.0001% and 10% (0.000001 to 0.1 parts per part of meat) based on the weight of the meat and usually containing between about $10^8$ to $10^{15}$ cells per ml, is added to the meat mixture as soon as it is ground. Preferably the composition is used at a level of $10^6$ to $10^8$ bacteria per gram of meat. Also preferably the bacterial concentrate described previously containing at least about $10^9$ cells per ml is used. Sausage prepared in this manner is stuffed into casings and preferably fermented at a temperature of 41° F. to 125° F. (5° C. to 52° C.) for periods of about six (6) hours or more depending upon the concentration of culture used. In the preferred process of the present invention, the ratio of *Micrococcus varians* to lactic acid bacteria by bacterial count is between 1 to 1 and 1 to 8.

SPECIFIC DESCRIPTION

Concentrates

Culture concentrates of *Micrococcus varians* were prepared as follows:

1. A culture medium consisting of 3% (by weight) dextrose, 2% yeast extract and 0.5% N-Z Amine Type B (Sheffield Chemical) was prepared in a 14 liter fermenter. The medium was heated to 250° F. (121.1° C.) and held at that temperature for 15 minutes. The medium was cooled to 90° F. (32.2° C.) and was inoculated with 0.75% (by volume) of an 18 to 20 hour broth mother *Micrococcus varians* culture which had been incubated at 90° F. (32.2° C.).

2. The culture was incubatd at 90° F. (32.2° C.) for 18 hours and the medium was neutralized to pH 6.8 to 7.0 with anhydrous ammonia gas. The fermentation mixture was vigorously aerated which produced final cell counts of about $2 \times 10^9$.

3. The bacteria are preferably not separated from the culture medium. The bacteria can be separated by centrifugation, reverse osmosis, ultrafiltraton and the like. The bacteria were mixed with sterile unspent growth medium to maintain their viability upon storage. Ten percent (10%) by weight of sterile glycerol was added to the resuspended bacterial concentrate as a freezing stabilizing agent.

4. The concentrate was quick-frozen and stored at $-25°$ F. ($-31°$ C.).

Culture concentrates of *Pediococcus cerevisiae* were prepared in the same manner with constant neutralization and usually concentration by removal of some of the growth medium. Other lactic acid producing bacterial concentrates can be prepared in the same manner as is well known to those skilled in the art.

The frozen concentrates preferably include a freezing stabilizing agent, such as glycerol and other such compounds which are well known to those skilled in the art. Unspent nutrient medium supplementing medium already present from growth is preferably provided with the bacteria for storage stability. Freezing is usually at less than $-20°$ C. and can be lowered to $-196°$ C. The frozen concentrates preferably are provided in dosage units of between 50 and 500 grams to the sausage maker.

Sausages

Curing and fermentation of the meat mixture in preparing sausage is accomplished in a manner known to the prior art. If the meat mixture is to be pre-cured, the curing may follow established procedures and this involved keeping the preparation at a temperature of 36° to 38° F. (2.2° to 3.3° C.) for a short period of time (4 hours or less) to allow some of the edible nitrates to undergo bacterial reduction to nitrite which under acid conditions along with any added nitrite produces nitric oxide which effects the cure to produce the bright red sausage color.

The cured meat preparation mixed with the bacteria is stuffed in the casing which is traditionally associated with the particular type of dry or semi-dry sausage. The encased sausage may or may not be smoked depending on its particular type and the conventional practice.

If the specific product being made is a "dry" sausage, the sausages are hung in drying rooms in which fermentation takes place within the sausage. In the United States there may be a preliminary fermentation at 98.6° to 104° F. (37° C. to 40° C.). The rooms are then kept at 50° F. to 80° F. (10° to 26.6° C.) temperature and high initial relative humidity above 80% and thereafter at 65 to 80% relative humidity, to assure that the saussage will dry from the inside outward.

If the specific product is a "semi-dry" sausage, the sausages would be moved into a smoke house or other suitable room or cabinet and are warmed, with or without an intermediate "tempering" period, to 80° to 125° F. (26.6° to 52° C.) internal temperature with high humidities, i.e. 75-95% relative humidity.

The fermentation period for dry sausage may be from 2 days to 10 days with a drying period of up to four months to obtain the desired water activity of the sausage. The semi-dry sausage may be fermented for 6 to 36 hours depending upon the temperature used and the final pH desired. The semi-dry sausage after fermentation is normally heated in a smoke house or other suitable room to an internal temperature which destroys trichinae which may be present in the pork and to denature the meat proteins. Smoke may be applied during all, part or none of the fermentation period or subsequent to fermentation for the dry and semi-dry sausage, depending upon the nature of the specific sausage being produced.

*Micrococcus varians* produces desirable flavors on a controlled basis which results in the unique flavor characteristic of sausage particularly dry sausage in combination with the lactic acid producing bacteria. The final pH of sausage is between about 4.8 and 5.4. This pH may vary considerably depending upon the type of product produced and the taste requirements of the area where the sausage is to be consumed. The pH of the sausage can be controlled by using selected mixtures of the bacteria in various ratios.

The following is an illustrative Example I of the present invention along with a comparative Example II.

EXAMPLE I

*Micrococcus varians* ATCC 15306 was combined with *Pediococcus cerevisiae* NRRL-B-5627 in a ratio of 25 to 75 parts by cell count. The concentrate was blended into the meat mixture. The meat mixture was stuffed into a known fibrous casing (Union Carbide $2 \times 30$ D.S.$_{t.m.}$) using a Vogt$_{t.m.}$ upright stuffer. The exterior of the casing was washed with a 2% solution of potassium sorbate as an antimycotic agent. The meat fermentation was initially at 80° F. (26.7° C.) and then lowered to 60° F. (15.6° C.). The meat formulation was:

| | |
|---|---|
| Pork Butts | 15.9 kg. |
| Beef Chuck | 6.8 kg. |
| Salt (3½%) | 757 g. |
| Sodium nitrite (150 ppm) | 3.5 g. |
| Dextrose | 175 g. |
| Isoascorbic acid | 12.4 g. |
| Genoa salami spice | 113 g. |

The results of the fermentation are shown in Table I:

TABLE I[(1)]

| Time | pH[(2)] |
|---|---|
| 22 hrs. | 5.55 |
| 41 hrs. | 5.16 |
| Lowered temperature to 60° F., 75% Room Humidity | |
| 3.7 days | 5.00 |
| 7.7 days | 5.00 |
| 19.0 days[(3)] | 5.00 |
| 32.0 days[(4)] | 5.00 |

[(1)]3.5 ml of $0.5 \times 10^9$ cells/ml *Micrococcus varians* and 4.5 ml of $20 \times 10^9$ cells/ml *Pediococcus cerevisiae*.
[(2)]The pH was determined by removing about 30 grams of meat from the casing and adding 60 ml of distilled water with blending. The pH was determined electrometrically.
[(3)]H$_2$O - 41.58 percent Fat - 27.98 percent
[(4)]H$_2$O - 33.23 percent Fat - 25.53 percent The product had a taste panel hedonic scale rating of 7.17 (rating between 1 and 9) when tested by 15 people. This is regarded as a very good rating. The color of the sausage was red and it had the proper firmness. The level of sodium nitrite is what is conventionally used and yet it appeared to have little bacteriostatic effect on the fermentation by the *Micrococcus varians*.

EXAMPLE II (COMPARATIVE)

Fifty-five (55) ml of culture containing $0.6 \times 10^9$ cells of *Micrococcus varians* (ATCC 15306) per ml were thoroughly blended into the meat mixture of Example I and stuffed into the casing using the procedure of Example I.

The sausage was hung in an incubator set at 21° C. and 93% relative humidity for 48 hours. The relative humidity was lowered to 90% for an additional 48 hours. Then the temperature was lowered to 17° C. and the relative humidity was reduced to 86%. These conditions were maintained for 48 hours and then the relative humidity was reduced to 72% for the remaining drying period. These fermentation conditions are even more favorable than those of Example I.

At the end of 28 days the sausage was evaluated for tang, color and flavor. The result was an unacceptable product with no flavor, poor color (gray) and no tang. Table II shows the very poor acid forming characteristics of *Micrococcus varians* as a function of time.

TABLE II

|  | Control | *Micrococcus varians* ATCC 15306 |
|---|---|---|
| pH Day 1 | 5.60 | 5.60 |
| pH Day 4 | 5.60 | 5.60 |
| pH Day 5 | 5.60 | 5.60 |
| pH Day 6 | 5.60 | 5.60 |
| pH Day 7 | 5.60 | 5.55 |
| pH Day 8 | 5.60 | 5.50 |

Clearly *Micrococcus varians* is a very poor acid producer and will not in itself produce good sausage.

There is a difference in flavor produced by the bacterial compositions of the present invention which are particularly desirable. Flavors are difficult to evaluate objectively but are very important commercially.

We claim:
1. The bacterial concentrate which comprises:
   (a) *Micrococcus varians* having the identifying characteristics of *Micrococcus varians* NRRL-B-11,060 (ATCC 15,306); and
   (b) between about 0.01 and 100 parts by bacterial count of a lactc acid producing bacterium which ferments in meat to lower the pH to less than about 5.4 to above about 4.8 per part by bacterial count of the Micrococcus wherein the concentrate contains at least about $1 \times 10^9$ bacteria cells per ml, nutrient medium and is frozen to less than about $-20°$ C.
2. The composition of claim 1 which contains a bacterial freezing stabilizing agent which maintains viability of the bacteria.
3. The composition of claim 1 in dosage units of between about 50 to 500 grams.
4. The concentrate of claim 1 wherein the lactic acid producing bacterium is *Pediococcus cerevisiae*.
5. The composition of claim 4 wherein the *Pediococcus cerevisiae* is strain NRRL-B-5627.

* * * * *